(12) United States Patent
Jacobs et al.

(10) Patent No.: US 6,502,575 B1
(45) Date of Patent: Jan. 7, 2003

(54) INSTRUMENT FOR INTERRUPTING CONDUCTION PATHS WITHIN THE HEART

(76) Inventors: Clemens J. Jacobs, Veenlanden 40, 3871 RD Hoevelaken (NL); Tjong Hauw Sie, Prinses Julianastraat 49, 8019 at Zwolle (NL)

(*) Notice: Subject to any disclaimer, the term of this patent is extended or adjusted under 35 U.S.C. 154(b) by 28 days.

(21) Appl. No.: 09/583,303

(22) Filed: May 30, 2000

Related U.S. Application Data

(62) Division of application No. 09/180,124, filed as application No. PCT/NL97/00223 on Apr. 25, 1997, now Pat. No. 6,165,174.

(30) Foreign Application Priority Data

May 3, 1996 (NL) .............................................. 1003024

(51) Int. Cl.[7] .............................................. A61B 19/00
(52) U.S. Cl. ...................... 128/898; 606/41; 607/122
(58) Field of Search ............ 606/31, 41; 607/100–105, 607/122; 600/374; 128/898

(56) References Cited

U.S. PATENT DOCUMENTS

| | | | |
|---|---|---|---|
| 5,348,554 A | * | 9/1994 | Imran et al. .................. 606/41 |
| 5,487,385 A | * | 1/1996 | Avitall ......................... 600/374 |
| 5,733,280 A | | 3/1998 | Avitall |
| 5,782,828 A | * | 7/1998 | Chen et al. .................... 606/42 |
| 5,797,960 A | * | 8/1998 | Stevens et al. ............. 606/213 |
| 6,237,605 B1 | * | 5/2001 | Vaska et al. ................. 128/898 |

OTHER PUBLICATIONS

Elvan et al, "Radiofrequency Catheter Ablation of the Atria Reduces Inducibility and Duration of Atrial Fibrillation in Dogs", Circulation, vol. 91, No. 8, Apr. 15, 1995, pp. 2235–2244.

Avitall et al, "A Thorascopic Approach to Ablate Atrial Fibrillation Via Linear Radiofrequency Lesion Generation on the Epicardium of Both Atria", NAPSE Abstracts, PACE, vol. 19, No. 241, Apr. 1996.

* cited by examiner

Primary Examiner—Michael Peffley
(74) Attorney, Agent, or Firm—Akerman Senterfitt

(57) ABSTRACT

A description is given of a probe for making strip-shaped transmural lesions in one or more walls of the atria of the heart in open-heart surgery. The stripe-shaped lesion blocks electrical impulses in a direction crosswise to the lesion. The probe has a handle (1), a closed end (2) and a relatively rigid shaft (5), and means (6, 7) for coupling the probe to an RF power source.

105 Claims, 3 Drawing Sheets

INSTRUMENT FOR INTERRUPTING CONDUCTION PATHS WITHIN THE HEART

CROSS REFERENCE TO RELATED APPLICATION

This is a Divisional of application Ser. No. 09/180,124 filed Nov. 2, 1998 now U.S. Pat. No. 6,165,174, filed Apr. 25, 1997, which is a 371 of PCT/NL97/00223.

FIELD OF THE INVENTION

The invention relates to an instrument for making at least one stripe-shaped transmural lesion in one or more walls of the atria of the heart, which lesion essentially blocks the electrical impulse conduction in a direction crosswise to the stripe-shaped transmural lesion.

BACKGROUND OF THE INVENTION

All kinds of heart arrhythmias, and in particular chronic and paroxysmal atrial fibrillation, can currently be treated by surgery.

A known surgical procedure (MAZE) was designed to eliminate atrial fibrillation permanently. In this procedure incisions are made with a scalpel in the walls of the atria, in order to block, by the thus formed interruption of the tissue continuity electrical impulse conduction in a direction crosswise to the incisions. As a result of the subsequent scarring, these electrical blocks acquire a permanent character.

This known technique is as yet performed only to a limited extent worldwide, owing co the complexity of the operation. The increased risk is particularly associated with the duration of the operation and the way in which the operation has to be carried out.

The duration of the operation, and in particular the cross-clamp time (x-clamp) is so long that there is a great risk of damage to the heart muscle.

The cross-clamp time required for the MAZE procedure alone is currently still an average of 68 min. (range 50–102 min.), and the necessary time on the heart-lung machine is on average 182 min. (range 130–256 min.). For further data you are referred to Atrial Fibrillations: Mechanisms and Therapeutic Strategies, Futura Publishing Co. Inc. Armonk, N.Y. 1994. J. L. Cox: Surgical Interruption of Atrial Reentry as a Cure for Atrial Fibrillation. The way in which the operation is performed with the scalpel produces an increased risk of vascular suture leaks and subsequent bleeding, due to the large number and location of the vascular sutures involved.

SUMMARY OF THE INVENTION

The object of the present invention is to provide instrument of the abovementioned type which eliminates the abovementioned disadvantages, and which in particular shortens the time required for the operation and reduces the risk of bleeding and damage, therefore reducing the risk for the patient in open-heart surgery.

According to the invention, the instrument indicated is characterized in that the instrument is a probe in which the end which during the operation comes into contact with the wall to be treated is a closed electrode which can interact with an RF power source, while the Probe is of a relatively rigid type.

The instrument according to the invention is a probe by means of which in open-heart surgery it is possible to make a permanent change in an atrial wall which is transmural, i.e. it extends over the entire thickness of the wall.

As will be discussed at a later stage, during the performance of the operation the electrode at the end of the probe is brought into contact with the atrial wall to be treated and is moved along it in a linear pattern. On excitation of the electrode with RF power, dielectric (RF) heating of the wall tissue occurs. The RF treatment produces a change in the cell structure of the atrial wall, with the result that electrical impulse conduction in a direction crosswise to the transmural lesion is blocked.

In order to be able to work well with it, the probe must be of a relatively rigid type, so that the electrode can be accurately positioned on and moved along the atrial wall. In the operation no disintegration of the tissue of the atrial wall occurs, and there is no risk of subsequent bleeding. The operation can be carried out on the outside or the inside of the atrium as desired.

Methods of RF heating or dielectric heating are based on the use of heat generated in materials which are relatively poor electrical conductors when they are placed in high-frequency electromagnetic fields. The heat is generated as a result of dielectric losses occurring in a material situated between metal electrodes which form a capacitor which is connected to a high-frequency (RF) generator. Such heating is highly uniform and therefore extremely suitable for use of the instrument, the probe, according to the invention. During use of the probe, one of the capacitor "plates" is formed by the electrode at the end of the probe, while the other "plate" is a counter-electrode which is stuck on, for example, the patient's back; when the latter electrode is being placed, it is preferable to use a contact gel which has electrical conductance. Of course, the counter-electrode can also be placed on the outside of the atrial wall of the heart, for example if the electrode of the probe is being brought into contact with the inside of said wall.

In connection with the invention, reference is made to WO 95/03742, which discloses a catheter comprising at the distal a metal electrode by means of which tissue erosion, also known as ablation, can be carried out.

Such a catheter typically has a length of approximately 1 meter, a diameter of approximately 2 mm, and has an electrode of approximately 2 mm diameter, and its low thickness makes it very flexible, so that it can follow a blood vessel without any problems. This catheter is suitable for local punctate ablation. Such a catheter is not suitable for use as a probe for making stripe-shaped transmural lesions in an atrial wall.

In particular, the probe according to the invention has at least a handle; an end; a relatively rigid shaft between the handle and the end, and connecting and conduction means for connecting the end of the probe to an RF power source.

In the instrument according to the invention a temperature recorder is advantageously present near the end of the probe, which temperature recorder, operating in a feedback system with the RF power source, can regulate the temperature of the end of the probe to a preset value. Through input of the RF power, the temperature of the end of the probe will generally rise; feedback with the RF power source makes it possible to ensure that the temperature of the end does not exceed a predetermined value.

With use of RF power it is extremely important that the fewest possible electrical blockages should be present in the body section between the end of the probe and the counter-electrode on the outside of the body. On account of this, it is preferable to ensure that the probe can interact with means for supplying a physiologically acceptable liquid to the end thereof. In its simplest form, such a liquid is supplied near the electrode of the probe by way of a line which does not form part of the probe. The function of the liquid is, on the one hand, to cool the electrode and, on the other, to prevent the occurrence of electrically insulating air gaps. which adversely affect the efficiency of the RF action.

It is very advantageous for the probe according to the invention itself to have means for discharging a physiologically acceptable liquid near the end of the probe. Said liquid will generally preferably have a certain degree of electrical conduction, and is expediently a physiological salt solution.

In a very attractive embodiment, the instrument has between the handle of the probe and the shaft inlet means for introducing the physiologically acceptable liquid, which inside the shaft remains electrically insulated from the connecting and conduction means present in the shaft, while near the end it has outflow means for the physiologically acceptable liquid. With this embodiment, the functioning of the probe can be improved yet further, and it can be ensured that the greatest RF energy effect is concentrated in the wall of the atrium to be treated, forming the desired transmural lesion.

At the side of the handle facing away from the end of the probe, the conduction and connecting means of the probe according to the invention comprise a connector connected thereto, with contact means for connection of the electrode to the end of the probe and the temperature recorder present therein to the RF power source.

The connector is preferably of the rapid coupling type, so that easy coupling to the RF power source is permitted.

In order to make handling of the instrument according to the invention, in the form of a probe, as easy as possible for the operating surgeon during an open-heart operation, the shaft of the probe preferably has an intrinsic curvature, which is expediently approximately 140°.

BRIEF DESCRIPTION OF THE DRAWINGS

The invention will now be explained with reference to the drawing, in which.

DETAILED DESCRIPTION OF THE DRAWINGS

Figure 1:
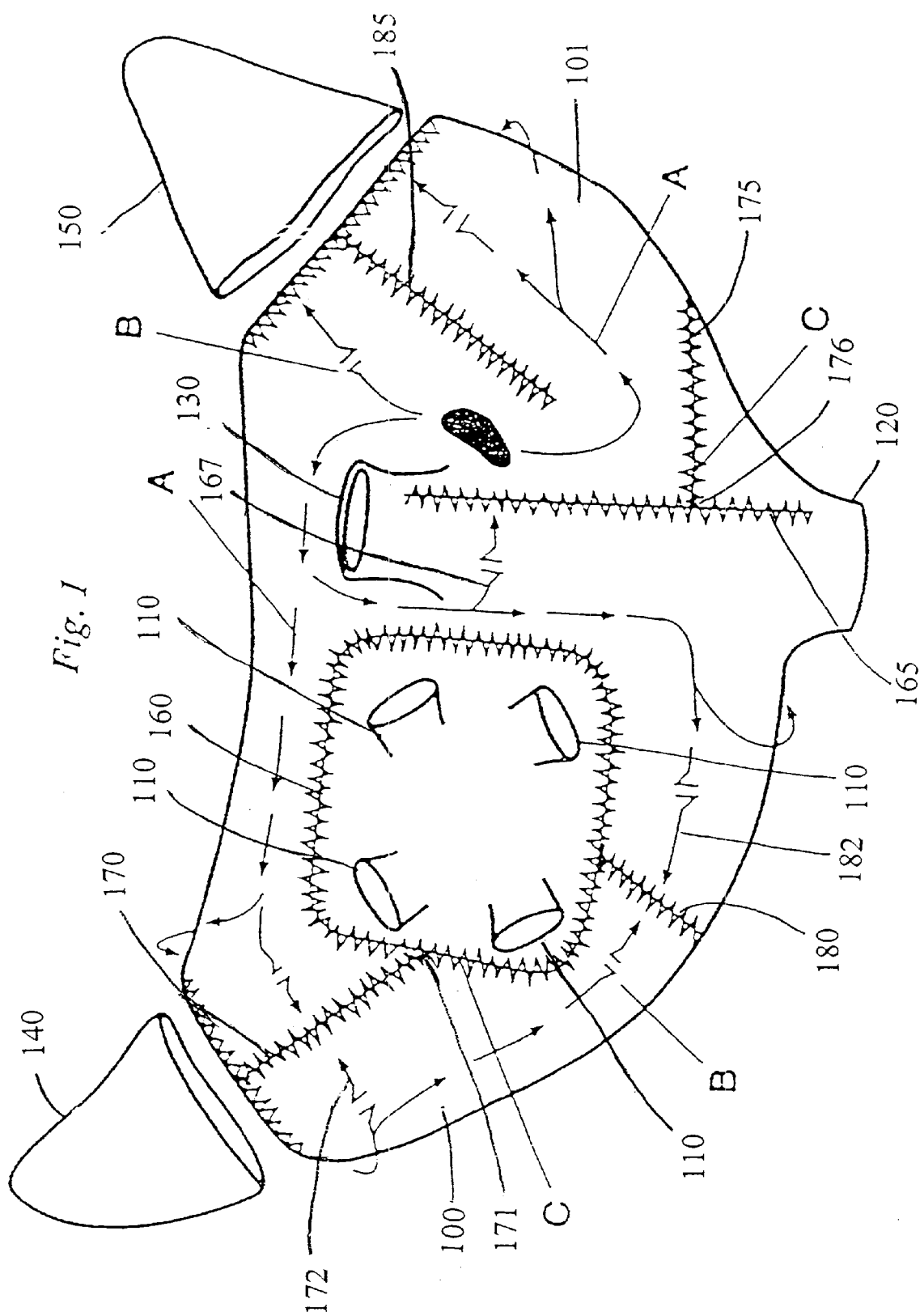
FIG. 1 shows a schematic picture of the transmural lesions which can be made with the instrument according to the invention, and which can block electrical impulses in directions crosswise to said lesions.

FIG. 1 shows diagrammatically in a two-dimensional view the two atria of a human heart, in which the transmural lesions are indicated by reference letter C, the undisturbed electrical impulses by A, and the blocked electrical impulses by B. The lesions C are in the nature of scar tissue which is formed after treatment using the probe according to the invention. The atria, as viewed epicardially, include the left atrium 100 and the right atrium 101. Structural features of the atria include the pulmonary veins 110, the inferior vena cava 120, the superior vena cava 130, the left atrial appendage 140 and the right atrial appendage 150. A first lesion 160 is a curved lesion that is joined end-to-end such that it encircles the pulmonary veins 110, and is between the pulmonary veins 110 and conductive pathways in the left atrium 100 and between the pulmonary veins 110 and conductive pathways in the right atrium 101. A second lesion 165 extends between the superior vena cava 130 and the inferior vena cava 120 and blocks a first conductive pathway 167. A third lesion 170 extends across the left atrium 100 from an intersection 171 with a portion of the first lesion 160 toward the left atrial appendage 140 and blocks a second conductive pathway 172. A fourth lesion 175 extends along the right atrium 101 laterally from an intersection 176 with a portion of the second lesion 165. A fifth lesion 180 extends from a portion of the first lesion 160 along the left atrium 100 and blocks a third conductive pathway 182. A sixth lesion 185 extends along the right atrium 101 toward the right atrial appendage 150.

Figure 2:
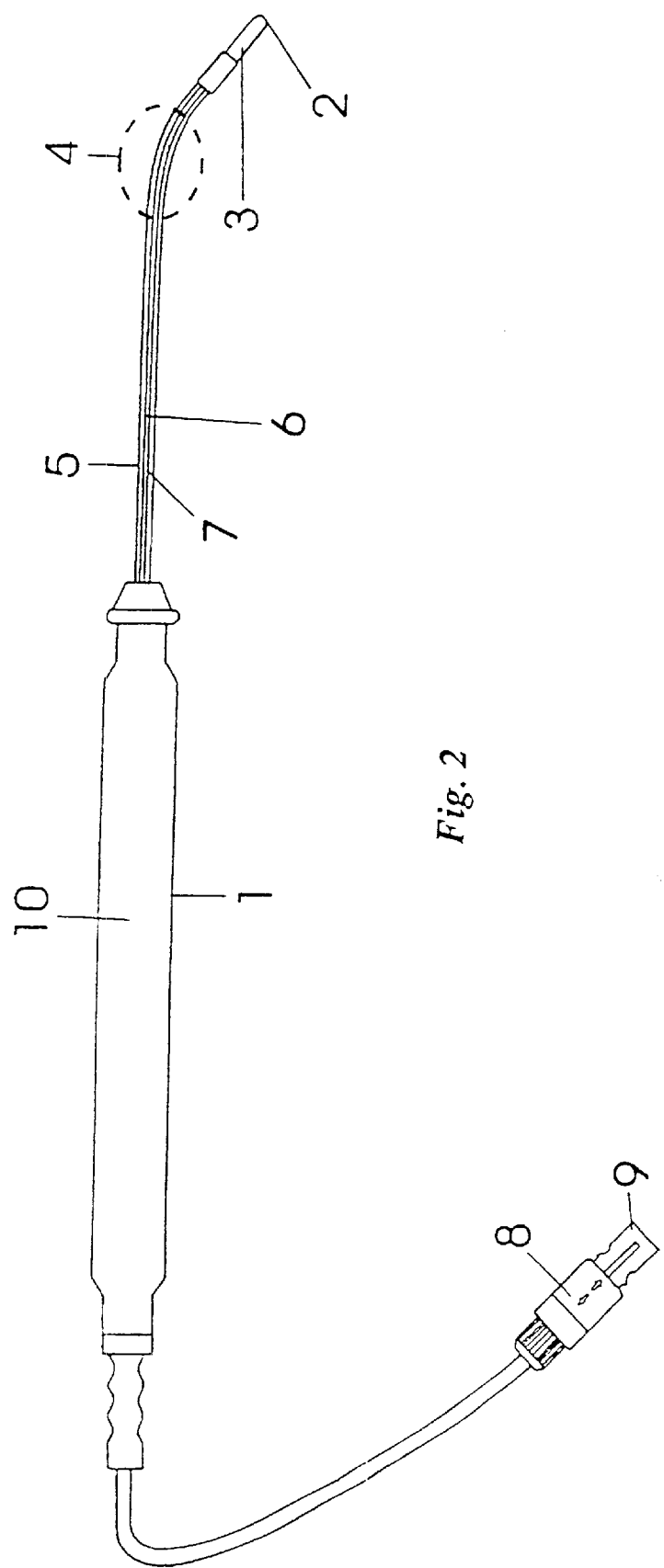
FIG. 2 shows an instrument according to the invention in a first embodiment.

FIG. 2 shows a probe according to the invention in a first embodiment, and shows a handle 1, an active metal end 2 as a closed electrode with indication of the position of a temperature sensor 3. The shaft of the probe 5 has a curvature 4 of approximately 140°, and inside the shaft run the electrical wires 6 for exciting the closed electrode-type end 2 and wire 7 for connecting the temperature sensor which is fitted at the position of reference number 3.

Inside the handle 1 are electrical switch means 10 (not shown in any further detail) for permitting connection of the probe to the RF generator (not shown). Reference numbers 8 and 9 also indicate a connector making it possible to couple the probe to the RF generator.

Figure 3:
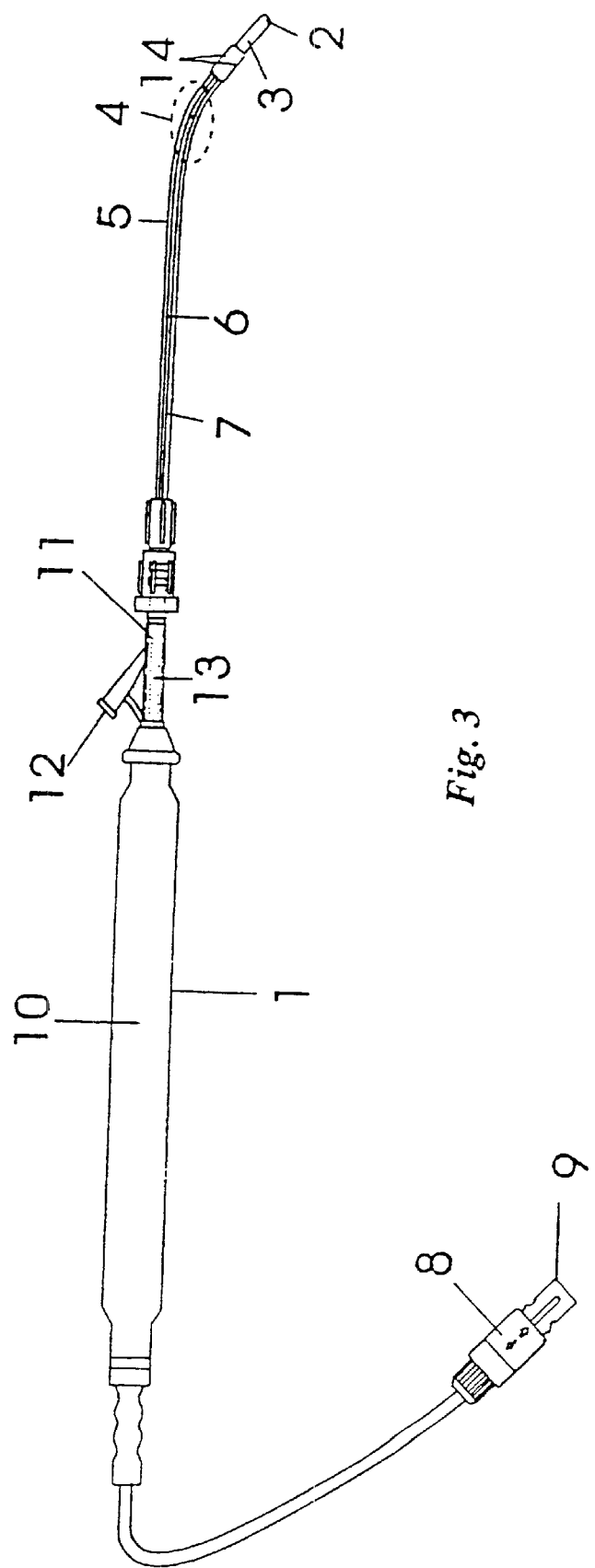
FIG. 3 shows an instrument according to the invention in a second embodiment.

FIG. 3 shows a particularly advantageous embodiment of the probe according to the invention, which is identical to the probe of FIG. 2, but in which reference number 11 indicates a Y-connector which makes it possible to supply a physiologically acceptable liquid by way of a port 12 into the shaft 5, said physiologically acceptable liquid being guided through the shaft 5 without contact with the conduction means 6 and 7. The physiologically acceptable solution flows by way of the port 12 to an inner shaft 13, and from there by way of the shaft 5 to the outflow ports 14 which are disposed in the vicinity of the metal end 2. The physiologically acceptable liquid is expediently a physiological salt solution which is readily tolerated by the body.

The physiological salt solution, on the one hand, achieves cooling of the closed electrode 2 and, on the other hand, lowers the electrical resistance between the closed electrode of the end 2 and the atrial wall. Extremely good and reproducible results are obtained with the probe shown in the figure. The source of RF power is typically a generator which can deliver a power of, for example, maximum 50 watt at a frequency of 500 kHz. The power supplied is a function of the temperature set and the tissue contact of the electrode forming the end of the probe. The desired temperature can be set at the generator, and in general lies in the range 50 to 70° C. If temperatures higher than the given range are permitted, burning of the tissue (coagulation) will occur, with the result that an insulating layer is formed; said layer will make further action of the RF energy difficult, with the result that underlying tissue is not treated fully, if at all.

The end 2 of the probe expediently comprises platinum and is typically a cylindrical shape with a diameter of 4 mm. The diameter can generally lie between 3 and 6 mm.

The total length of the probe without connection means is typically approximately 35 cm, the handle being approximately 20 cm long, the shaft approximately 10 cm, and the end approximately 2 cm. In general, the length of the shaft 5 lies between 8 and 15 cm, and the shaft has a diameter between 3 and 6 mm and is made of a physiologically acceptable plastic. Suitable plastics are nylon 66, polypropylene and high-density polyethylene.

What is claimed is:

1. A method of using a surgical instrument for making at least one stripe-shaped transmural conduction blocking lesion in an atrium wall of a heart, the method comprising the steps of:

providing a surgical instrument having a handle and an electrode affixed substantially rigidly to the handle;

providing an RF power source in electrical connection with the electrode;

contacting an outside portion of the atrium wall with the electrode; and transferring a sufficient amount of RF energy from the RF power source through the surgical instrument to the outside portion of the atrium wall to cause a stripe-shaped, transmural conduction blocking lesion to form in the atrium wall.

2. The method of claim 1, wherein the atrium is contacted with the surgical instrument at a plurality of locations on the atrium wall, and wherein RF energy is applied at each of the plurality of locations to cause a plurality of transmural conduction blocking lesions to form in the atrium wall.

3. The method of claim 1, further comprising the steps of:

providing an animal having a thoracic cavity containing the heart having an atrium; and surgically opening the thoracic cavity of the animal to expose the heart.

4. The method of claim 3, wherein the animal is a human being.

5. The method of claim 1, wherein the surgical instrument comprises a probe having:

a handle;

a closed electrode at one end of the probe;

a connection and conduction means electrically communicating with the electrode and adapted for connecting the electrode to an RF power source;

a shaft connecting the handle and the electrode, the shaft being more rigid than a catheter which is adapted for following a blood vessel;

a temperature recorder at the end of the probe with the electrode, the temperature recorder being adapted to operatively communicate with a feedback system and the RF power source such that the temperature of the electrode can be regulated to a preset value; and means for supplying a physiologically acceptable liquid to the electrode, the means for supplying the liquid being connected to the shaft.

6. The method of claim 3, wherein the surgical instrument comprises a probe having:

a handle;

a closed electrode at one end of the probe;

a connection and conduction means electrically communicating with the electrode and adapted for connecting the electrode to an RF power source;

a shaft connecting the handle and the electrode, the shaft being more rigid than a catheter which is adapted for following a blood vessel;

a temperature recorder at the end of the probe with the electrode, the temperature recorder being adapted to operatively communicate with a feedback system and the RF power source such that the temperature of the electrode can be regulated to a preset value; and means for supplying a physiologically acceptable liquid to the electrode, the means for supplying the liquid being connected to the shaft.

7. The method of claim 3, further comprising a step of making a transmural incision in the atrium.

8. The method of claim 7, wherein the step of contacting the atrium wall with the surgical instrument is performed by inserting the surgical instrument through the transmural incision such that the surgical instrument contacts the inner surface of the atrium wall.

9. A method of treating an arrhythmia in the heart of a patient by RF treatment of the atrium of the heart comprising:

(a) providing a surgical instrument having a handle and an electrode affixed substantially rigidly to the handle;

(b) providing an RF power source in electrical connection with the electrode;

(c) contacting a portion of the outside wall of the atrium with the electrode;

(d) transferring a sufficient amount of RF energy from the RF power source to the electrode to cause a lesion to form in the portion of the wall of the atrium;

(e) moving the electrode along the outside wall of the atrium into contact with another portion of the outside wall of the atrium;

(f) transferring a sufficient amount of RF energy from the RF power source to the electrode to cause a lesion to form in the another portion of the wall of the atrium; and (g) repeating steps (c) to (f) to form at least one end-to-end, encircling, continuous transmural lesion in the atrium around at least one pulmonary vein.

10. The method of claim 9 wherein the electrode is moved along the outside atrial wall without lifting the electrode away from the wall.

11. The method of claim 9 wherein the RF energy is transferred to the electrode as the electrode is moved along the outside atrial wall.

12. The method of claim 9 wherein the electrode is also moved in a linear pattern to form a second, substantially linear transmural lesion intersecting with the encircling lesion.

13. The method of claim 9 wherein the encircling lesion encircles all of the heart's pulmonary veins.

14. The method of claim 9 wherein a portion of the encircling lesion is formed between a pulmonary vein and conductive pathways in the right atrium.

15. The method of claims 9 wherein a portion of the encircling lesion is formed between a pulmonary vein and conductive pathways in the left atrium.

16. A method of treating an arrhythmia in the heart of a patient by RF treatment of the atrium of the heart comprising:

(a) providing a surgical instrument having a handle and an electrode affixed substantially rigidly to the handle;

(b) providing an RF power source in electrical connection with the electrode;

(c) contacting a portion of the outside wall of the atrium with the electrode;

(d) transferring a sufficient amount of RF energy from the RF power source to the electrode to cause a lesion to form in the portion of the wall of the atrium;

(e) moving the electrode along the outside wall of the atrium into contact with another portion of the outside wall of the atrium;

(f) transferring a sufficient amount of RF energy from the RF power source to the electrode to cause a lesion to form in the another portion of the wall of the atrium; and (g) repeating steps (c) to (f) to form at least one curved, continuous transmural lesion in the atrium between a pulmonary vein and conductive pathways in the left atrium.

17. The method of claim 16 wherein the electrode is moved along the outside atrial wall without lifting the electrode away from the wall.

18. The method of claim 16 wherein the RF energy is transferred to the electrode as the electrode is moved along the outside atrial wall.

19. The method of claim 16 wherein the electrode is also moved in a linear pattern to form a second, substantially linear transmural lesion intersecting with the curved lesion.

20. The method of claim 16 wherein the curved lesion extends around at least one pulmonary vein.

21. The method of claim 20 wherein the curved lesion extends around all of the heart's pulmonary veins.

22. The method of claim 16 also comprising at least one curved, continuous transmural lesion formed in the atrium between a pulmonary vein and conductive pathways in the right atrium.

23. A method of treating an arrhythmia in the heart of a patient by RF treatment of the atrium of the heart comprising:
   (a) providing a surgical instrument having a handle and an electrode affixed substantially rigidly to the handle;
   (b) providing an RF power source in electrical connection with the electrode;
   (c) contacting a portion of the outside wall of the atrium between a pulmonary vein and conductive pathways in the left atrium with the electrode;
   (d) transferring a sufficient amount of RF energy from the RF power source to the electrode to cause a curved, continuous, transmural lesion to form in the portion of the wall of the atrium.

24. The method of claim 23 wherein the RF energy is transferred by moving the electrode along the outside atrial wall without lifting the electrode away from the wall.

25. The method of claim 23 wherein the RF energy is also transferred to the atrium to form at least one additional, substantially linear transmural lesion intersecting with the curved lesion.

26. The method of claim 23 wherein the lesion extends around all of the heart's pulmonary veins.

27. The method of claim 23 also comprising contacting a second portion of the outside wall of the atrium between a pulmonary vein and conductive pathways in the right atrium with the electrode and transferring a sufficient amount of RF energy from the RF power source to the electrode to cause a curved, continuous, transmural lesion to form in the second portion of the wall of the atrium.

28. A method of treating an arrhythmia in the heart of a patient by RF treatment of the atrium of the heart comprising:
   (a) providing a surgical instrument having a handle and an electrode affixed substantially rigidly to the handle;
   (b) providing an RF power source in electrical connection with the electrode;
   (c) contacting a portion of the outside wall of the atrium adjacent a pulmonary vein with the electrode;
   (d) transferring a sufficient amount of RF energy from the RF power source to the electrode to form an end-to-end, encircling, continuous transmural lesion in the atrium around at least one pulmonary vein.

29. The method of claim 28 wherein the RF energy is transferred by moving the electrode along the outside atrial wall without lifting the electrode away from the wall.

30. The method of claim 28 wherein the RF energy is also transferred to the atrium to form at least one additional, substantially linear transmural lesion intersecting with the encircling lesion.

31. The method of claim 28 wherein the lesion extends around all of the heart's pulmonary veins.

32. A method of treating an arrhythmia in the heart of a patient by RF treatment of the atrium of the heart comprising:
   (a) providing a surgical instrument having a handle and an electrode affixed substantially rigidly to the handle;
   (b) providing an RF power source in electrical connection with the electrode;
   (c) contacting a portion of the outside wall of the atrium with the electrode;
   (d) transferring a sufficient amount of RF energy from the RF power source to the electrode to cause a lesion to form in the portion of the wall of the atrium;
   (e) moving the electrode along the outside wall of the atrium into contact with another portion of the outside wall of the atrium without lifting the electrode away from the wall;
   (f) transferring a sufficient amount of RF energy from the RF power source to the electrode as the electrode is moved to form at least one curved, continuous, transmural lesion in the atrium.

33. The method of claim 32 further comprising moving the electrode to form a second, substantially linear transmural lesion intersecting with the curved lesion.

34. The method of claims 32 wherein a portion of the curved lesion is formed between a pulmonary vein and conductive pathways in the left atrium.

35. The method of claim 33 wherein the second lesion formed extends across the left atrium toward the left atrial appendage.

36. The method of claim 32 wherein the curved lesion is formed between a pulmonary vein and the right atrium.

37. The method of claim 32 wherein the curved lesion is formed between a pulmonary vein and the left atrium.

38. A method of treating an arrhythmia in the heart of a patient by RF treatment of the atrium of the heart comprising:
   (a) providing a surgical instrument having a handle, an electrode affixed substantially rigidly to the handle, and a liquid outflow near the electrode;
   (b) providing an RF power source in electrical connection with the electrode;
   (c) contacting a portion of the outside wall of the atrium with the electrode;
   (d) transferring a sufficient amount of RF energy from the RF power source to the electrode in combination with delivery of a physiologically acceptable liquid to cause a lesion to form in the portion of the wall of the atrium;
   (e) moving the electrode along the outside wall of the atrium into contact with another portion of the outside wall of the atrium;
   (f) transferring a sufficient amount of RF energy from the RF power source to the electrode in combination with delivery of a physiologically acceptable liquid to cause a lesion to form in the another portion of the wall of the atrium; and
   (g) repeating steps (c) to (f) to form at least one end-to-end, encircling, continuous transmural lesion in the atrium around at least one pulmonary vein.

39. The method of claim 38 wherein the electrode is moved along the outside atrial wall without lifting the electrode away from the wall.

40. The method of claim 38 wherein the RF energy is transferred to the electrode as the electrode is moved along the outside atrial wall.

41. The method of claim 38 wherein the electrode is also moved in a linear pattern to form a second, substantially linear transmural lesion intersecting with the encircling lesion.

42. The method of claim 38 wherein the encircling lesion encircles all of the heart's pulmonary veins.

43. The method of claim 38 wherein a portion of the encircling lesion is formed between a pulmonary vein and conductive pathways in the right atrium.

44. The method of claims 38 wherein a portion of the encircling lesion is formed between a pulmonary vein and conductive pathways in the left atrium.

45. The method of claim 38 wherein the physiologically acceptable liquid is a salt solution.

46. A method of treating an arrhythmia in the heart of a patient by RF treatment of the atrium of the heart comprising:
    (a) providing a surgical instrument having a handle, an electrode affixed substantially rigidly to the handle, and a liquid outflow near the electrode;
    (b) providing an RF power source in electrical connection with the electrode;
    (c) contacting a portion of the outside wall of the atrium with the electrode;
    (d) transferring a sufficient amount of RF energy from the RF power source to the electrode in combination with delivery of a physiologically acceptable liquid to cause a lesion to form in the portion of the wall of the atrium;
    (e) moving the electrode along the outside wall of the atrium into contact with another portion of the outside wall of the atrium;
    (f) transferring a sufficient amount of RF energy from the RF power source to the electrode in combination with delivery of a physiologically acceptable liquid to cause a lesion to form in the another portion of the wall of the atrium; and
    (g) repeating steps (c) to (f) to form at least one curved, continuous transmural lesion in the atrium between a pulmonary vein and conductive pathways in the left atrium.

47. The method of claim 46 wherein the electrode is moved along the outside atrial wall without lifting the electrode away from the wall.

48. The method of claim 46 wherein the RF energy is transferred to the electrode as the electrode is moved along the outside atrial wall.

49. The method of claim 46 wherein the electrode is also moved in a linear pattern to form a second, substantially linear transmural lesion intersecting with the curved lesion.

50. The method of claim 46 wherein the curved lesion extends around at least one pulmonary vein.

51. The method of claim 50 wherein the curved lesion extends around all of the heart's pulmonary veins.

52. The method of claim 46 also comprising at least one curved, continuous transmural lesion formed in the atrium between a pulmonary vein and conductive pathways in the right atrium.

53. The method of claim 46 wherein the physiologically acceptable liquid is a salt solution.

54. A method of treating an arrhythmia in the heart of a patient by RF treatment of the atrium of the heart comprising:
    (a) providing a surgical instrument having a handle, an electrode affixed substantially rigidly to the handle, and a liquid outflow near the electrode;
    (b) providing an RF power source in electrical connection with the electrode;
    (c) contacting a portion of the outside wall of the atrium between a pulmonary vein and conductive pathways in the left atrium with the electrode,
    (d) transferring a sufficient amount of RF energy from the RF power source to the electrode in combination with delivery of a physiologically acceptable liquid to cause a curved, continuous, transmural lesion to form in the portion of the wall of the atrium.

55. The method of claim 54 wherein the RF energy is transferred by moving the electrode along the outside atrial wall without lifting the electrode away from the wall.

56. The method of claim 54 wherein the RF energy is also transferred to the atrium to form at least one additional, substantially linear transmural lesion intersecting with the curved lesion.

57. The method of claim 54 wherein the lesion extends around all of the heart's pulmonary veins.

58. The method of claim 54 also comprising contacting a second portion of the outside wall of the atrium between a pulmonary vein and conductive pathways in the right atrium with the electrode and transferring a sufficient amount of RF energy from the RF power source to the electrode in combination with delivery of a physiologically acceptable liquid to cause a curved, continuous, transmural lesion to form in the second portion of the wall of the atrium.

59. The method of claim 54 wherein the physiologically acceptable liquid is a salt solution.

60. A method of treating an arrhythmia in the heart of a patient by RF treatment of the atrium of the heart comprising:
    (a) providing a surgical instrument having a handle, an electrode affixed substantially rigidly to the handle, and a liquid outflow near the electrode;
    (b) providing an RF power source in electrical connection with the electrode;
    (c) contacting a portion of the outside wall of the atrium adjacent a pulmonary vein with the electrode;
    (d) transferring a sufficient amount of RF energy from the RF power source to the electrode in combination with delivery of a physiologically acceptable liquid to form an end-to-end, encircling, continuous transmural lesion in the atrium around at least one pulmonary vein.

61. The method of claim 60 wherein the RF energy is transferred by moving the electrode along the outside atrial wall without lifting the electrode away from the wall.

62. The method of claim 60 wherein the RF energy is also transferred to the atrium to form at least one additional, substantially linear transmural lesion intersecting with the encircling lesion.

63. The method of claim 60 wherein the lesion extends around all of the heart's pulmonary veins.

64. The method of claim 54 wherein the physiologically acceptable liquid is a salt solution.

65. A method of treating an arrhythmia in the heart of a patient by RF treatment of the atrium of the heart comprising:
    (a) providing a surgical instrument having a handle, an electrode affixed substantially rigidly to the handle and a liquid outflow near the electrode;
    (b) providing an RF power source in electrical connection with the electrode;
    (c) contacting a portion of the outside wall of the atrium with the electrode;
    (d) transferring a sufficient amount of RF energy from the RF power source to the electrode in combination with delivery of a physiologically acceptable liquid to cause a lesion to form in the portion of the wall of the atrium;

(e) moving the electrode along the outside wall of the atrium into contact with another portion of the outside wall of the atrium without lifting the electrode away from the wall;

(f) transferring a sufficient amount of RF energy from the RF power source to the electrode in combination with delivery of a physiologically acceptable liquid as the electrode is moved to form at least one curved, continuous, transmural lesion in the atrium.

66. The method of claim 65 further comprising moving the electrode to form a second, substantially linear transmural lesion intersecting with the curved lesion.

67. The method of claims 65 wherein a portion of the curved lesion is formed between a pulmonary vein and conductive pathways in the left atrium.

68. The method of claim 66 wherein the second lesion formed extends across the left atrium toward the left atrial appendage.

69. The method of claim 65 wherein the curved lesion is formed between a pulmonary vein and the right atrium.

70. The method of claim 65 wherein the curved lesion is formed between a pulmonary vein and the left atrium.

71. The method of claim 54 wherein the physiologically acceptable liquid is a salt solution.

72. A method of treating an arrhythmia in the heart of a patient by RF treatment of the atrium of the heart comprising:
(a) providing a surgical instrument having a handle, an electrode affixed substantially rigidly to the handle, and a temperature sensor adjacent the electrode;
(b) providing an RF power source in electrical connection with the electrode;
(c) contacting a portion of the outside wall of the atrium with the electrode;
(d) transferring a sufficient amount of RF energy from the RF power source to the electrode at a sensed temperature in the range of 50 to 70 degrees C. to cause a lesion to form in the portion of the wall of the atrium;
(e) moving the electrode along the outside wall of the atrium into contact with another portion of the outside wall of the atrium;
(f) transferring a sufficient amount of RF energy from the RF power source to the electrode at a sensed temperature in the range of 50 to 70 degrees C. to cause a lesion to form in the another portion of the wall of the atrium; and
(g) repeating steps (c) to (f) to form at least one end-to-end, encircling, continuous transmural lesion in the atrium around at least one pulmonary vein.

73. The method of claim 72 wherein the electrode is moved along the outside atrial wall without lifting the electrode away from the wall.

74. The method of claim 72 wherein the RF energy is transferred to the electrode as the electrode is moved along the outside atrial wall.

75. The method of claim 72 wherein the electrode is also moved in a linear pattern to form a second, substantially linear transmural lesion intersecting with the encircling lesion.

76. The method of claim 73 wherein the encircling lesion encircles all of the heart's pulmonary veins.

77. The method of claim 72 wherein a portion of the encircling lesion is formed between a pulmonary vein and conductive pathways in the right atrium.

78. The method of claims 72 wherein a portion of the encircling lesion is formed between a pulmonary vein and conductive pathways in the left atrium.

79. The method of claim 72 wherein the temperature of the electrode during the transfer of electrical energy is limited to a regulated preset value in the range of 50 to 70 degrees C.

80. A method of treating an arrhythmia in the heart of a patient by RF treatment of the atrium of the heart comprising:
(a) providing a surgical instrument having a handle, an electrode affixed substantially rigidly to the handle, and a temperature sensor adjacent the electrode;
(b) providing an RF power source in electrical connection with the electrode;
(c) contacting a portion of the outside wall of the atrium with the electrode;
(d) transferring a sufficient amount of RF energy from the RF power source to the electrode at a sensed temperature in the range of 50 to 70 degrees C. to cause a lesion to form in the portion of the wall of the atrium;
(e) moving the electrode along the outside wall of the atrium into contact with another portion of the outside wall of the atrium;
(f) transferring a sufficient amount of RF energy from the RF power source to the electrode at a sensed temperature in the range of 50 to 70 degrees C. to cause a lesion to form in the another portion of the wall of the atrium; and
(g) repeating steps (c) to (f) to form at least one curved, continuous transmural lesion in the atrium between a pulmonary vein and conductive pathways in the left atrium.

81. The method of claim 80 wherein the electrode is moved along the outside atrial wall without lifting the electrode away from the wall.

82. The method of claim 80 wherein the RF energy is transferred to the electrode as the electrode is moved along the outside atrial wall.

83. The method of claim 80 wherein the electrode is also moved in a linear pattern to form a second, substantially linear transmural lesion intersecting with the curved lesion.

84. The method of claim 80 wherein the curved lesion extends around at least one pulmonary vein.

85. The method of claim 84 wherein the curved lesion extends around all of the heart's pulmonary veins.

86. The method of claim 80 also comprising at least one curved, continuous transmural lesion formed in the atrium between a pulmonary vein and conductive pathways in the right atrium.

87. The method of claim 80 wherein the temperature of the electrode during the transfer of electrical energy is limited to a regulated preset value in the range of 50 to 70 degrees C.

88. A method of treating an arrhythmia in the heart of a patient by RF treatment of the atrium of the heart comprising:
(a) providing a surgical instrument having a handle, an electrode affixed substantially rigidly to the handle, and a temperature sensor adjacent the electrode;
(b) providing an RF power source in electrical connection with the electrode;
(c) contacting a portion of the outside wall of the atrium between a pulmonary vein and conductive pathways in the left atrium with the electrode;
(d) transferring a sufficient amount of RF energy from the RF power source to the electrode at a sensed temperature in the range of 50 to 70 degrees C. to cause a curved, continuous, transmural lesion to form in the portion of the wall of the atrium.

89. The method of claim 88 wherein the RF energy is transferred by moving the electrode along the outside atrial wall without lifting the electrode away from the wall.

90. The method of claim 88 wherein the RF energy is also transferred to the atrium to form at least one additional, substantially linear transmural lesion intersecting with the curved lesion.

91. The method of claim 88 wherein the lesion extends around all of the heart's pulmonary veins.

92. The method of claim 88 also comprising contacting a second portion of the outside wall of the atrium between a pulmonary vein and conductive pathways in the right atrium with the electrode and transferring a sufficient amount of RF energy from the RF power source to the electrode at a sensed temperature in the range of 50 to 70 degrees C. to cause a curved, continuous, transmural lesion to form in the second portion of the wall of the atrium.

93. The method of claim 88 wherein the temperature of the electrode during the transfer of electrical energy is limited to a regulated preset value in the range of 50 to 70 degrees C.

94. A method of treating an arrhythmia in the heart of a patient by RF treatment of the atrium of the heart comprising:.
  (a) providing a surgical instrument having a handle, an electrode affixed substantially rigidly to the handle, and a temperature sensor adjacent the electrode;
  (b) providing an RF power source in electrical connection with the electrode;
  (c) contacting a portion of the outside wall of the atrium adjacent a pulmonary vein with the electrode;
  (d) transferring a sufficient amount of RF energy from the RF power source to the electrode at a sensed temperature in the range of 50 to 70 degrees C. to form an end-to-end, encircling, continuous transmural lesion in the atrium around at least one pulmonary vein.

95. The method of claim 94 wherein the RF energy is transferred by moving the electrode along the outside atrial wall without lifting the electrode away from the wall.

96. The method of claim 94 wherein the RF energy is also transferred to the atrium to form at least one additional, substantially linear transmural lesion intersecting with the encircling lesion.

97. The method of claim 94 wherein the lesion extends around all of the heart's pulmonary veins.

98. The method of claim 94 wherein the temperature of the electrode during the transfer of electrical energy is limited to a regulated preset value in the range of 50 to 70 degrees C.

99. A method of treating an arrhythmia in the heart of a patient by RF treatment of the atrium of the heart comprising:
  (a) providing a surgical instrument having a handle, an electrode affixed substantially rigidly to the handle, and a temperature sensor adjacent the electrode;
  (b) providing an RF power source in electrical connection with the electrode;
  (c) contacting a portion of the outside wall of the atrium with the electrode;
  (d) transferring a sufficient amount of RF energy from the RF power source to the electrode at a sensed temperature in the range of 50 to 70 degrees C. to cause a lesion to form in the portion of the wall of the atrium;
  (e) moving the electrode along the outside wall of the atrium into contact with another portion of the outside wall of the atrium without lifting the electrode away from the wall;
  (f) transferring a sufficient amount of RF energy from the RF power source to the electrode at a sensed temperature in the range of 50 to 70 degrees C. as the electrode is moved to form at least one curved, continuous, transmural lesion in the atrium.

100. The method of claim 99 further comprising moving the electrode to form a second, substantially linear transmural lesion intersecting with the curved lesion.

101. The method of claims 99 wherein a portion of the curved lesion is formed between a pulmonary vein and conductive pathways in the left atrium.

102. The method of claim 99 wherein the second lesion formed extends across the left atrium toward the left atrial appendage.

103. The method of claim 99 wherein the curved lesion is formed between a pulmonary vein and the right atrium.

104. The method of claim 99 wherein the curved lesion is formed between a pulmonary vein and the left atrium.

105. The method of claim 99 wherein the temperature of the electrode during the transfer of electrical energy is limited to a regulated preset value in the range of 50 to 70 degrees C.

* * * * *